US007069672B2

(12) United States Patent
Hahn

(10) Patent No.: US 7,069,672 B2
(45) Date of Patent: Jul. 4, 2006

(54) SHOE WITH A FOOT MASSAGING EFFECT

(76) Inventor: Matthias Hahn, Kurpfalzstr. 14, 67734 Katzweiler (DE)

(*) Notice: Subject to any disclaimer, the term of this patent is extended or adjusted under 35 U.S.C. 154(b) by 0 days.

(21) Appl. No.: 10/450,489

(22) PCT Filed: Dec. 11, 2001

(86) PCT No.: PCT/DE01/04708

§ 371 (c)(1),
(2), (4) Date: Oct. 30, 2003

(87) PCT Pub. No.: WO02/47601

PCT Pub. Date: Jun. 20, 2002

(65) Prior Publication Data

US 2004/0093766 A1 May 20, 2004

(30) Foreign Application Priority Data

Dec. 16, 2000 (DE) ................................ 100 62 929
Mar. 26, 2001 (DE) ................................ 101 14 859
Aug. 24, 2001 (DE) ................................ 101 41 568

(51) Int. Cl.
*A43B 7/06* (2006.01)
*A61F 5/14* (2006.01)

(52) U.S. Cl. .................. 36/141; 36/43; 36/44; 36/3 R; 36/3 B

(58) Field of Classification Search .................. 36/141, 36/43, 44, 3 R, 3 B, 3 A, 88, 28, 29
See application file for complete search history.

(56) References Cited

U.S. PATENT DOCUMENTS 2,441,879 A * 5/1948 Gantt .......................... 36/3 R
2,457,944 A * 1/1949 Vlastos .......................... 36/3 B
3,552,044 A * 1/1971 Wiele .......................... 36/71
4,674,203 A * 6/1987 Goller .......................... 36/44
4,823,799 A * 4/1989 Robbins .......................... 36/140
4,831,749 A * 5/1989 Tsai .......................... 36/3 B
4,846,159 A * 7/1989 Anzai et al. .......................... 601/128
4,910,882 A * 3/1990 Goller .......................... 36/3 B
4,970,807 A * 11/1990 Anderie et al. .......................... 36/28
4,997,295 A * 3/1991 Saitou .......................... 384/492
5,138,775 A * 8/1992 Chu .......................... 36/3 B
5,617,650 A * 4/1997 Grim .......................... 36/88
5,799,413 A * 9/1998 Argyris .......................... 36/43
5,860,229 A * 1/1999 Morgenstern .......................... 36/141
5,979,076 A * 11/1999 Li .......................... 36/3 B
6,061,928 A * 5/2000 Nichols .......................... 36/28
6,199,304 B1 * 3/2001 Ludemann .......................... 36/44
6,219,941 B1 * 4/2001 Kukoff .......................... 36/44

FOREIGN PATENT DOCUMENTS

EP 0100067 * 2/1984
EP 0383685 * 8/1990

* cited by examiner

*Primary Examiner*—M. D. Patterson
(74) *Attorney, Agent, or Firm*—Rader, Fishman & Grauer PLLC

(57) ABSTRACT

A shoe with a foot-massaging effect comprises a sole, optionally with a heel, and a top material. A cushion containing a massage element and/or active medical agents is provided in the interior of the shoe, above the sole, said cushion has a flexible base panel on the bottom, corresponding to the shape of the sole, and an elastic protective nonwoven fabric on the top, the latter being permanently connected to said base panel. A toe cap containing active medical agents can also be provided in the tip of the shoe. These measures result in a fairly significant foot-massaging effect and at the same time, enable the show to be used without creating an odor.

21 Claims, 7 Drawing Sheets

XX
XX
XXI
XXII

SHOE WITH A FOOT MASSAGING EFFECT

TECHNICAL FIELD

The invention generally relates to footwear and more particularly relates to shoes having a foot-massaging effect.

BACKGROUND OF THE INVENTION

Generally, shoes feature an inner sole with a smooth structure. Underneath, the inner sole is provided with a pad of minimal height at least in certain sections, e.g., in the area of the heel and/or the ball of the foot, in order to provide a "softer" step for the person wearing the shoe.

Furthermore, footwear is known that is designated as bathing shoes or slip-on shoes. Generally, these can be distinguished by a strap or crosspiece that runs over the top of the foot and which attaches the shoe to the person's foot. Such footwear often consists of extruded or foamed plastic and is often formed in one piece. Furthermore, there is footwear in the form of several pieces with a sole, e.g., consisting of leather or wood, and with a bump-like structure being formed on this sole. Due to the bump-like structure, when the person wearing the shoe walks, his or her sole is massaged by the bumps, which generates good, beneficial blood circulation in the feet of the person wearing the shoes.

Shoes with smooth inner soles are disadvantageous in that they exert absolutely no massaging effect on the feet of the person wearing the shoes. For shoes with bump-like, foot-massaging structures, the problem always arises that the intermediate spaces between the bumps can become filled with dirt particles. In addition, perspiration secreted by the foot can settle into these intermediate spaces. The substance formed by the dirt and perspiration between the bumps eventually leads to an unpleasant odor and possibly to foot diseases due to fungal bacteria, etc.

The problem of the invention is to create a shoe of the type mentioned in the introduction, which can produce a relatively strong foot-massaging effect and which simultaneously provides essentially odor- and dirt-free use of the shoe.

The problem is solved according to the invention by means of a pad, which is arranged in the interior of the shoe above the sole, which contains a massaging element and/or medicinal agents, and which consists of a flexible base plate adapted to the shape of the sole on the bottom side and on the top side an elastic protective nonwoven fabric rigidly connected to the base plate.

It is known that the sole of a person is divided into different reflex zones. Medically, there exists a direct connection between the individual foot reflex zones and the organs or body parts of the person. Targeted massaging at certain foot reflex zones has a direct effect on the health of the corresponding body part or organ. The pad containing the massaging element and/or medicinal agents provides continuous massaging of the sole of the person wearing the shoe while the shoe is on the foot. The continuous massaging of the sole of the person positively stimulates the well-being of the person. This can be realized especially well by the effect of the sole massage promoting blood circulation. The elastic nonwoven fabric, which is arranged on the top side of the massaging element and/or the medicinal agents and which is rigidly connected to the flexible base plate, prevents the penetration of foot perspiration and dirt into the pad, which provides for odor-free use of the shoe.

Preferably, a cap that releases medicinal agents is arranged at the shoe tip in the interior of the shoe. In this way, the medicinal agents can act on the toes of the person wearing the shoe. The medicinal agent can exert an effect, e.g., a perspiration-blocking function and/or a heating function. The cap containing the medicinal agents can be inserted into the interior of the shoe by the manufacturer during production or at a later time.

According to a first configuration of the shoe according to the invention, the massaging element is formed as a plurality of bumps, which are arranged on the base plate in uniform or offset rows. Just a plurality of regular or irregular bumps provides an especially effective massaging of the soles, because the heads of the bumps easily press into the soles at point contacts and the massaging effect is generated by the rolling of the foot during walking. Furthermore, the bumps are formed in one piece with the base plate. In this way, the base plate and the bumps are produced in a simple way, e.g., through injection molding. Advantageously, the bumps have the shape of hemispheres with their rounded part pointing into the interior of the shoe.

According to a second configuration of the invention, the massaging element is formed as a plurality of balls, which are arranged loosely and irregularly or in uniform or offset rows on the base plate. In principle, the balls have the same effect as the previously mentioned bumps; however, the balls can move in the pad of the shoe, which causes additional rolling of the balls as the foot rolls while the person wearing the shoe is walking, which has an additional stimulating effect on the sole. Depending on the arrangement of the balls in the pad, namely, loosely or irregularly or in uniform or offset rows, a different massaging effect of the sole can be achieved.

Preferably, the balls are embedded in an elastic material and/or connected together by an elastic material. The balls can be maintained for a long time without loss of the massaging effect on the sole both due to the embedding in the elastic material and also the connection to the elastic material, which is realized, e.g., by means of elastic crosspieces that connect to the ends of the balls. Here, the balls can be arranged in one plane with the shape of grapes.

Advantageously, the material of the balls and the elastic material exhibit the same or different Shore hardness values. The massaging effect of the soles can be influenced by the corresponding material pairing. Obviously, the elastic material can be totally different from the material used to produce the balls. Thus, the invention can deal with different materials.

In order to effectively counteract abrasion of the balls, preferably the balls are provided with a sliding coating on their surface. The sliding coating can be deposited, e.g., after production of the balls or set in the material during production of the balls. Obviously, the use of a sliding-promoting material for the production of the balls is also suitable.

For a refinement of the pad containing the balls, the heel contains a valve device, which is connected to the interior of the pad filled with the balls. Preferably, the valve device is formed as a one-way valve with ventilation openings formed in the upper material of the shoe. Because the balls in the interior of the pad constantly move and change their position while the person wearing the shoe is walking, a constant low pressure is created in the pad, which continuously changes its position within the pad while the person is walking. This can be perceived as pleasant or also as unpleasant by the person wearing the shoe. The valve now provides the possibility of suctioning surrounding air due to the low pressure in the pad while the person is walking as a compressed medium and guiding the air into the interior of the pad, so that a "softer" step is perceived by the person wearing the shoe. For each step, a high pressure is generated in the pad in turn at each pressure point, which is equalized by guiding air through the ventilation openings in the upper material of the shoe. While the person is walking, surrounding air is thus constantly suctioned, led into the interior of the pad, and then guided through the ventilation openings of the shoe. This realizes a doubled massaging effect, on the one hand, by the balls, and, on the other hand, by the unloaded positions of the pad filled with compressed air. The arrangement of a large air cushion and thus the effect of a "softer" step can also be supported by forming a flexible, expandable chamber in the heel between the ventilation device and the pad filled with balls. The flexible chamber features an increased volume for storing surrounding air, which creates an increase of the air volume in the pad containing the balls.

In order to prevent damage to the chamber formed in the heel of the shoe due to material wear and tear and use of the shoe, the flexible, expandable chamber is separated on the bottom side by a solid protective plate from the lower region of the heel or the sole. In this way, the heel arranged underneath the protective plate can be replaced when necessary.

If the pad arranged in the interior of the shoe is filled with medicinal agents, then the pad can be filled with medicinal agents by means of a valve device arranged in the heel. Here, this valve arrangement is likewise built as a one-way valve. Therefore, when necessary, a medicinal agent can be refilled, e.g., by means of a nozzle, when the agent has been partially or completely consumed over the course of time. In addition, an alternative medicinal agent can also be filled into the pad in order to achieve a different medical effect.

So that the medicinal agent located in the pad can be guided into the shoe interior and thus onto the sole of the person wearing the shoe, the protective nonwoven fabric has a plurality of small pores.

According to an alternative configuration of the shoe according to the invention, the pad is formed as an insert for loose insertion into the shoe. In this way, any shoe can be provided with a pad customized for the person wearing the shoe by inserting a corresponding insert into the shoe. If desired, the insert can also be removed or replaced by a different insert at any time.

Furthermore, the cap containing the medicinal agents can be inserted into the tip of the shoe separately or as a component of the pad formed as an insert. In this way, an insertion or exchange of the cap containing the medicinal agents is possible, likewise at any time, into and out of the shoe. Obviously, the cap is likewise provided with a plurality of small pores. Advantageously, the insert is formed with or without a footbed.

For another advantageous configuration of a pad provided with balls, a flexible spring band surrounds the pad on the inner edge of the pad. The flexible spring band enables a complete filling of the pad with balls, which are pressed into the flexible spring band at the edges due to loading while the person wearing the shoe is walking. Therefore, despite the total filling of the pad, the balls have a certain freedom of motion to generate the massaging effect.

Furthermore, as previously explained in general with reference to the shoe, the insert can also have a valve device, which is located in the region of the heel, which is formed as a one-way valve, and which is connected to the interior of the insert or the chamber, so that the insert can be provided with a compressed medium and also with a medicinal agent.

The bumps of the pad or the insert are further formed so that they are hollow and connected to the flexible chamber. Here, the head of each bump is formed as a pressure cap. Through this configuration of the bumps, a better massaging effect is achieved with the bump heads, which press into the sole of the person wearing the shoe under loading and return to their original position again after the loading.

In addition, the bumps can be assembled into several bump bands. This arrangement can produce very fine massaging effects on the soles of the person wearing the shoes. Preferably, the base plate of the pad has recesses in which the bump bands are placed so that the bands can move.

For another configuration of the shoe according to the invention, a motor is inserted in the heel of the sole. This motor has a driver arranged eccentric to the motor axis. The driver is connected flexibly to the bump bands. The motor can be turned on and off by means of a switch. An automatic start-up of the motor is also possible, e.g., due to loading or unloading of the heel of the shoe. The motor provides a massaging effect, in addition to that provided by the shape of the bumps, by moving the bump bands in the interior of the pad of the shoe back and forth. This back-and-forth motion is ensured by the eccentric arrangement of one or more drivers to the motor axis. Preferably, the motor is further operated by means of batteries, which are stored in the heel. Different massaging effects can be achieved by arranging the bump bands in the shoe in the longitudinal or perpendicular direction.

According to a third configuration of the shoe according to the invention, the massaging element includes a ball thread consisting of a continuous thread with balls loosely arranged in a line. This ball thread is inserted into the pad in the form of a spiral. This measure produces a defined guidance of the balls as the foot of the person wearing the shoe rolls while the person is walking, which has a positive effect on the massaging effect. Depending on the shape of the shoe and thus on the shape of the pad, at least one other thread equipped with loose balls is provided, and the ends of this thread are attached to the base plate or to the ball thread. In this way, practically the entire pad is filled with balls. For an alternative configuration, the massaging element includes rows arranged one next to the other each consisting of balls of a continuous thread loosely arranged in a line, with the ends of each thread attaching to the base plate. For both embodiments, a nonwoven fabric strip is preferably inserted in the edge regions of the pad not filled in by balls. The nonwoven fabric strips ensure a tight bundling of the balls.

For another configuration of the shoe according to the invention, the massaging element is formed as an elastic tube wound into a spiral shape, whose outer end is connected to an air inlet valve configured as a one-way valve and whose inner end is connected to a throttled air outlet. While the person wearing the shoe is walking, a low pressure is built up after time in the tube, and this low pressure opens the air inlet valve and thus guides air into the tube interior. Due to the throttled air outlet, this air can bleed out of the shoe interior only relatively slowly. In this way the tube produces a massaging effect on the sole. In order to provide free access of air to the air inlet valve, the air inlet valve is advantageously arranged behind an opening in the upright edge of the base plate.

It is understood that the previously mentioned features and the features still to be explained in the following can be used not only in the specified combination, but also in other combinations without leaving the scope of the present invention.

DETAILED DESCRIPTION OF THE PREFERRED EMBODIMENTS

Figures 1, 2, 3:
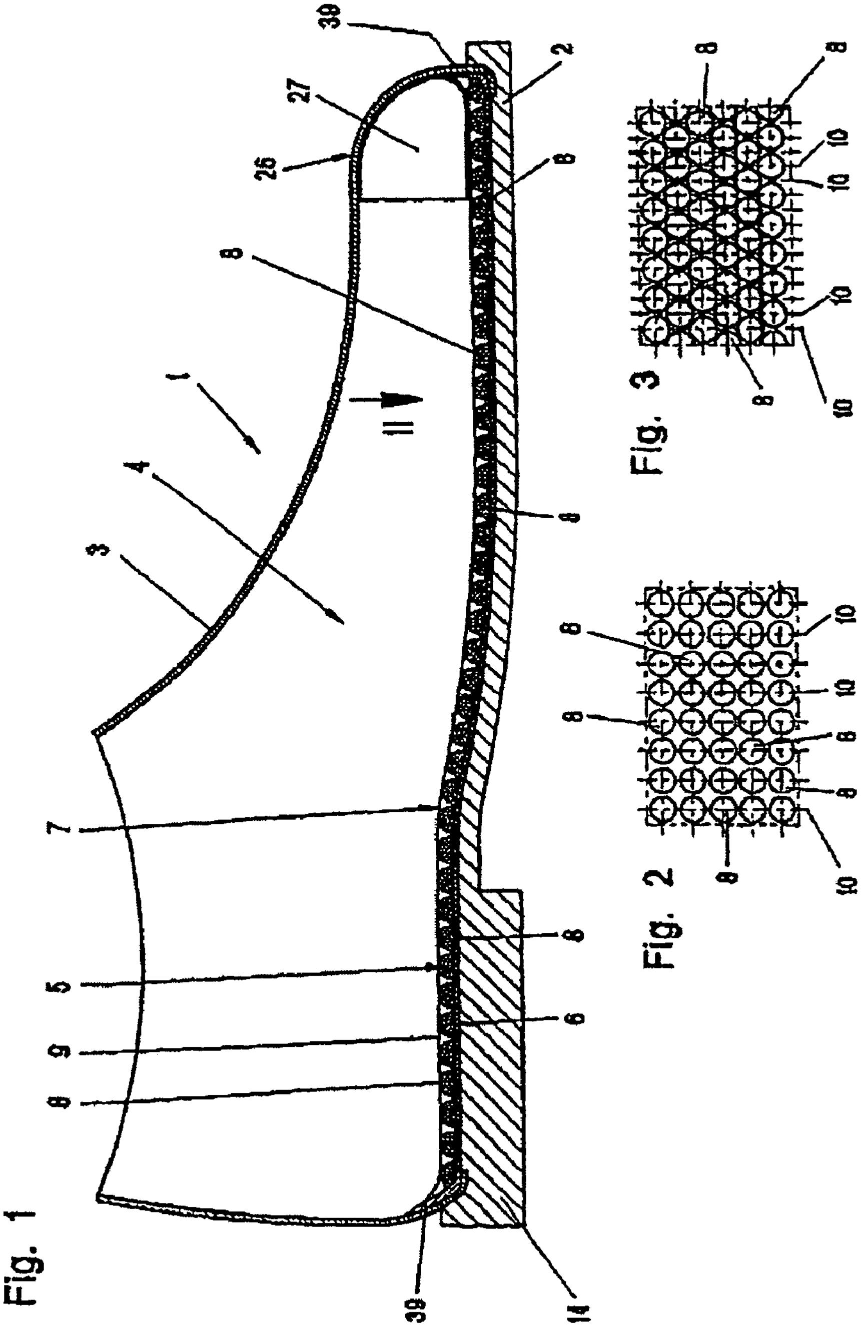
FIG. 1, a longitudinal section through a shoe according to the invention.
FIG. 2, a partial view of the illustration from FIG. 1 in the direction of the arrow II, FIG. 3, an alternative configuration of the illustration from FIG. 2, FIG. 4, a longitudinal section through a shoe according to the invention in an alternative configuration, FIG. 5, an enlarged illustration of detail V from FIG. 4 in an alternative configuration, FIG. 6, a longitudinal section through a shoe according to the invention in another alternative configuration, FIG. 7, a partial view of the illustration from FIG. 6 in the direction of arrow VII, FIG. 8, a longitudinal section through an insert for a shoe according to the invention, FIG. 9, a longitudinal section through an alternative insert for a shoe according to the invention, FIG. 10, an enlarged illustration of detail X from FIG. 9 under loading by the foot of a person wearing the shoe, FIG. 11, a partial section through a shoe according to the invention in another alternative embodiment, FIG. 12, an enlarged illustration of detail XII from FIG. 11, FIG. 13, a longitudinal section through a shoe according to the invention in another alternative configuration, FIG. 14, an enlarged illustration of detail XIV from FIG. 13, FIG. 15, an enlarged illustration of detail XV from FIG. 13 in an alternative embodiment, FIG. 16, an enlarged illustration of detail XVI from FIG. 13 in an alternative configuration, FIG. 17, a longitudinal section through a shoe according to the invention in another alternative configuration, FIG. 18, a partial view of the illustration from FIG. 17 in the direction of arrow XVIII, FIG. 19, an alternative configuration of the illustration from FIG. 18, FIG. 20, a section through the illustration from FIG. 19 according to line XX—XX, FIG. 21, an enlarged sectional illustration of detail XXI from FIG. 20, and FIG. 22, an enlarged sectional illustration of detail XXIII from FIG. 20.

FIG. 1 shows a section through a shoe 1, which has a sole 2 with a heel 14 and an upper material 3. The sole 2 and the upper material 3 are connected together in a known way. In the shoe interior 4 above the sole 2, there is a pad 5, which includes a flexible base plate 6 that is adapted to the shape of the sole 2 and forms the footbed 7. A plurality of bumps 8 are attached to the base plate 6 in the direction of the shoe interior 4. The bumps 8 have the shape of hemispheres with the rounded side pointing in the direction of the shoe interior 4. Above the bumps 8 there is an elastic protective nonwoven fabric 9, which contacts the bumps 8 and connects to the base plate 6 or the upper material 3 with a raised section 39 at the side. The bumps 8 consist of elastic material, so that they change their shape under loading and are restored to their original shape after unloading. In this way, the foot rolling in the shoe 1 while the person is walking is constantly massaged by the elastic bumps 8 changing their shape.

A cap 27 is inserted into the shoe tip 26. This cap contains a medicinal agent, e.g., against athlete's foot. The agent can be discharged from the cap through relatively small pores in the cap 27. The cap 27 is formed such that it is constantly spreading itself out. In this way, it is always in close contact with the protective nonwoven fabric 9 and the shoe tip 26.

According to FIG. 2, the bumps 8 are arranged on the base plate 6 in rows 10 one next to or behind another, whereby the foot presses in more between the bumps 8 producing a strong massaging effect. In contrast, the bumps 8 in FIG. 3 are arranged in offset rows 10. This produces a very fine massaging effect.

Figure 4:
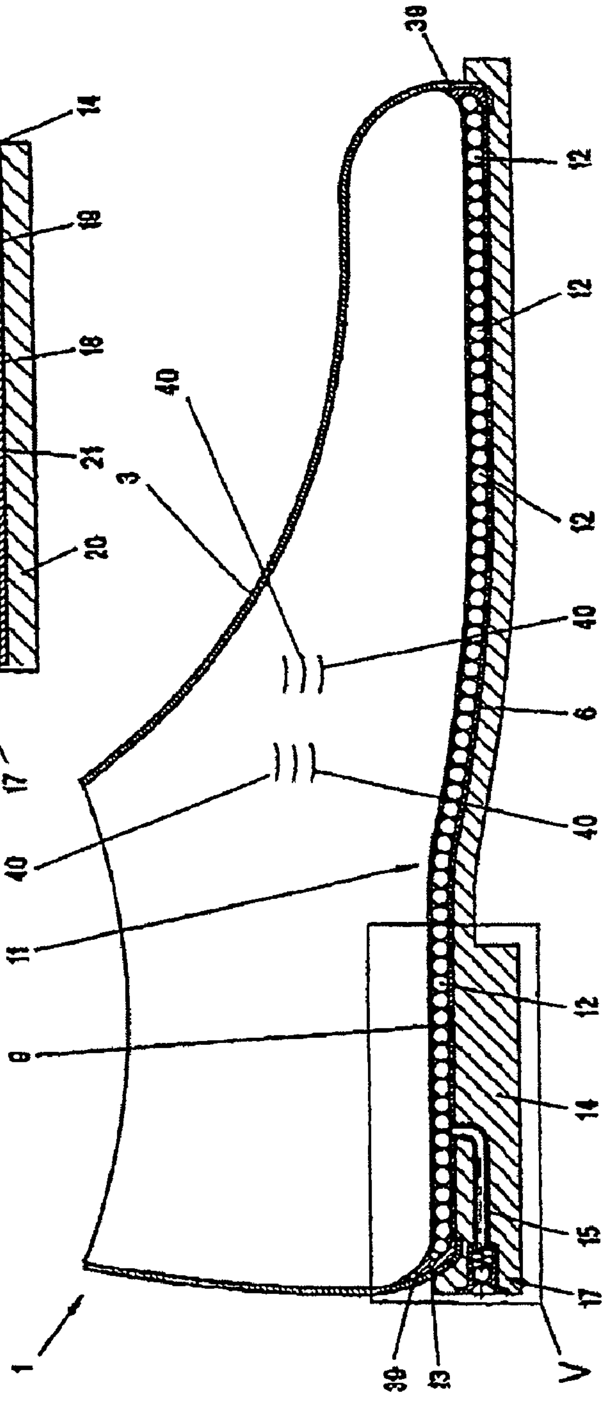

The shoe 1 according to FIG. 4 contains a pad 11, for which a plurality of balls 12 are arranged loosely on the base plate 6. Under loading, these balls are slightly displaced relative to each other and thus create a massaging effect. The base plate 6 and the protective nonwoven fabric 9 are connected rigidly and possess a transition 13 to the upper material 3.

Figure 5:
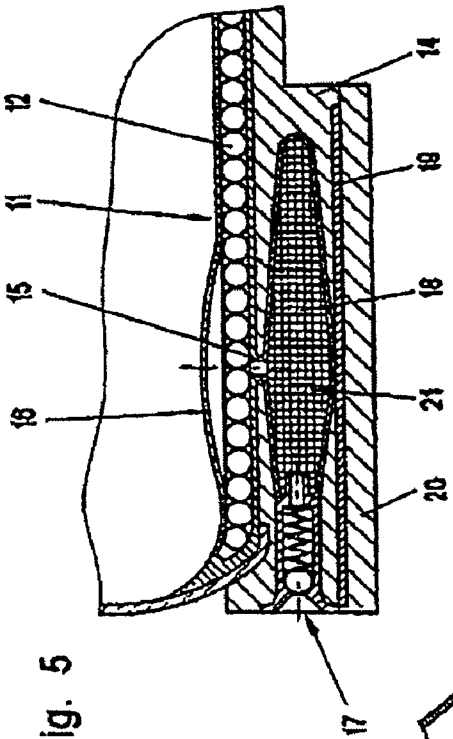

The pad 11 containing the balls 12 is completely sealed and has a feed 15 formed in the heel 14. At one end of the feed 15, there is a valve 17, which can be accessed from outside in the heel 14 and by means of which this pad 11 can be provided with a compressed medium. In this way, the protective nonwoven fabric 9 can bulge out at unloaded points 16, as shown in FIG. 5. Because the unloaded point 16 changes as the foot rolls in the shoe 1, a double massaging effect is produced, on the one hand, by the balls 12, and, on the other hand, by the unloaded point 16 itself. The upper material 3 of the shoe 1 includes ventilation openings 40, which are arranged like scales and are cut so that moisture and dirt falling from above cannot enter into the shoe 1. By means of the rolling foot movement, the air located in this pad 11 is discharged through the ventilation openings 40. This generates a low pressure in the pad 11, which is equalized by the valve 17, which is formed as a one-way valve, by means of air being suctioned through the valve 17 due to the low pressure and then guiding the air through the feed 15 into the pad 11.

For the embodiment according to FIG. 5, a chamber 18 is provided in the heel 14 between the valve 17 and the pad 11 containing the balls 12 with only a short feed 15 being provided. In the heel 14, the chamber 18 is protected at the bottom by a protective plate 19. The heel sole 20 located underneath the plate can be replaced. The chamber 18 is filled with a compressed medium 21, which bulges the nonwoven fabric when the protective nonwoven fabric 9 is at least partially unloaded. Loading increases the pressure in the chamber 18, which therefore expands. This sequence increases the massaging effect. Discharged air is replaced in the same way as explained in reference to FIG. 4. If necessary, however, air can also be refilled into the chamber 18 from time to time manually, e.g., with a suitable air pump.

Figures 6, 7:
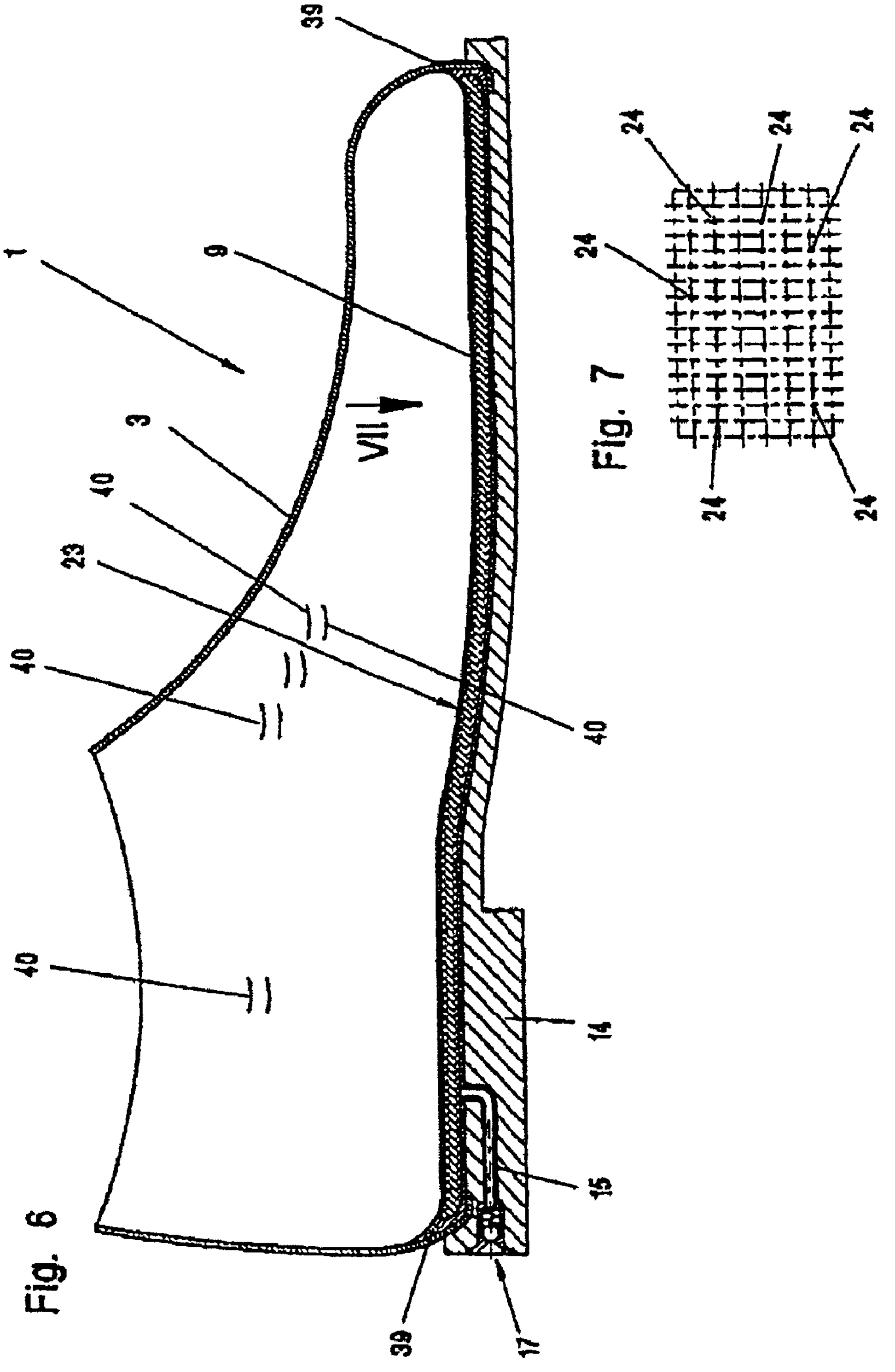

The shoe 1 according to FIG. 6 has a pad 23, which contains medicinal agents and which extends over the entire surface of the top side of the sole 2, which receives pressure from the foot. By means of the valve 17 present in the heel 14 and the feed 15, the medical pad 23 is filled with medicinal agents. Small pores 24 are worked into the protective nonwoven fabric 9, as can be seen from FIG. 7, by means of which the medicinal agent is led into the shoe interior 4.

Figures 8, 9, 10, 11, 12:
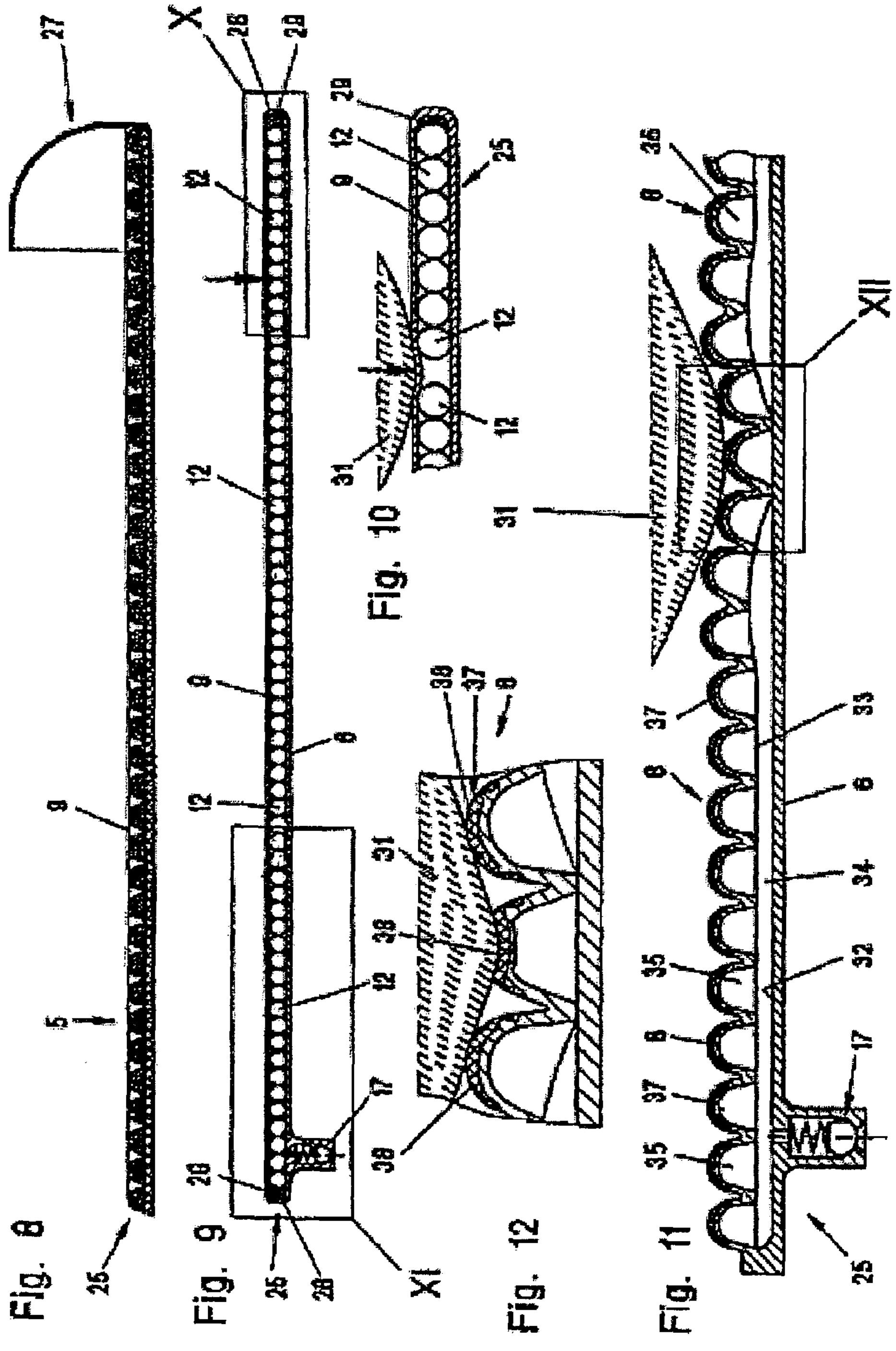

FIG. 8 shows an insert 25 for the shoe 1. The insert has a pad 5 with bumps 8 and a cap 27. Through this configuration, it is possible to buy normal shoes and then to realize both a massaging effect and also a medical effect with the insert 25.

For the insert 25 according to FIG. 9, the base plate 6 is connected to the protective nonwoven fabric 9 at a peripheral edge 28. Balls 12 are inserted all over in the insert 25. A surrounding spring band 29 is placed pointing from the peripheral edge 28 in the direction of the balls 12. The valve 17, by means of which the insert 25 can be provided with both a compressed medium, such as air, and also with a medicinal agent, is located in the region of the heel 14 of the shoe 1. For an alternative configuration that is not shown, the valve 17 can be eliminated, which allows the insert to be used for a normal shoe 1.

FIG. 10 shows a portion of the insert 25 under loading. The foot rolls on the protective nonwoven fabric 9 of the insert 25. Here, the main instantaneous load acts in the direction of the arrow through the foot region 31. In this region, the balls 12 are displaced, which presses the spring band 29 together. After the loading, the spring band 29 relaxes and pushes the balls 12 back into their original position. This produces a massaging effect for the foot both during loading and also during unloading.

FIG. 11 shows an insert 25 with elastic bumps 8 with a through chamber 34 provided between the inner side 32 of the base plate 6 and the lower side 33 of the bumps 8. The bumps 8 are hollow and their hollow region 35 is connected to the through chamber 34. On the outer side the bump head 36 has a pressure cap 37, which comes into contact with the foot region 31. In the region of the loading through the foot, the bumps 8 are pressed in the direction of the base plate 6 and their lower side 33 comes into contact with the inner side 32 of the base plate 6. For a decrease of the inner pressure, i.e., for a low pressure in the through chamber 34, the inner pressure can be increased again by means of the valve 17. As the compressed medium, both a gaseous material or a liquid can be used.

The pressure caps 37 according to FIG. 12 are designed as elastic disks 38. For strong loading, the bump heads 36 deform inwards and spring back outwards when unloaded. This increases the massaging effect even more.

Figures 13, 14, 15, 16:
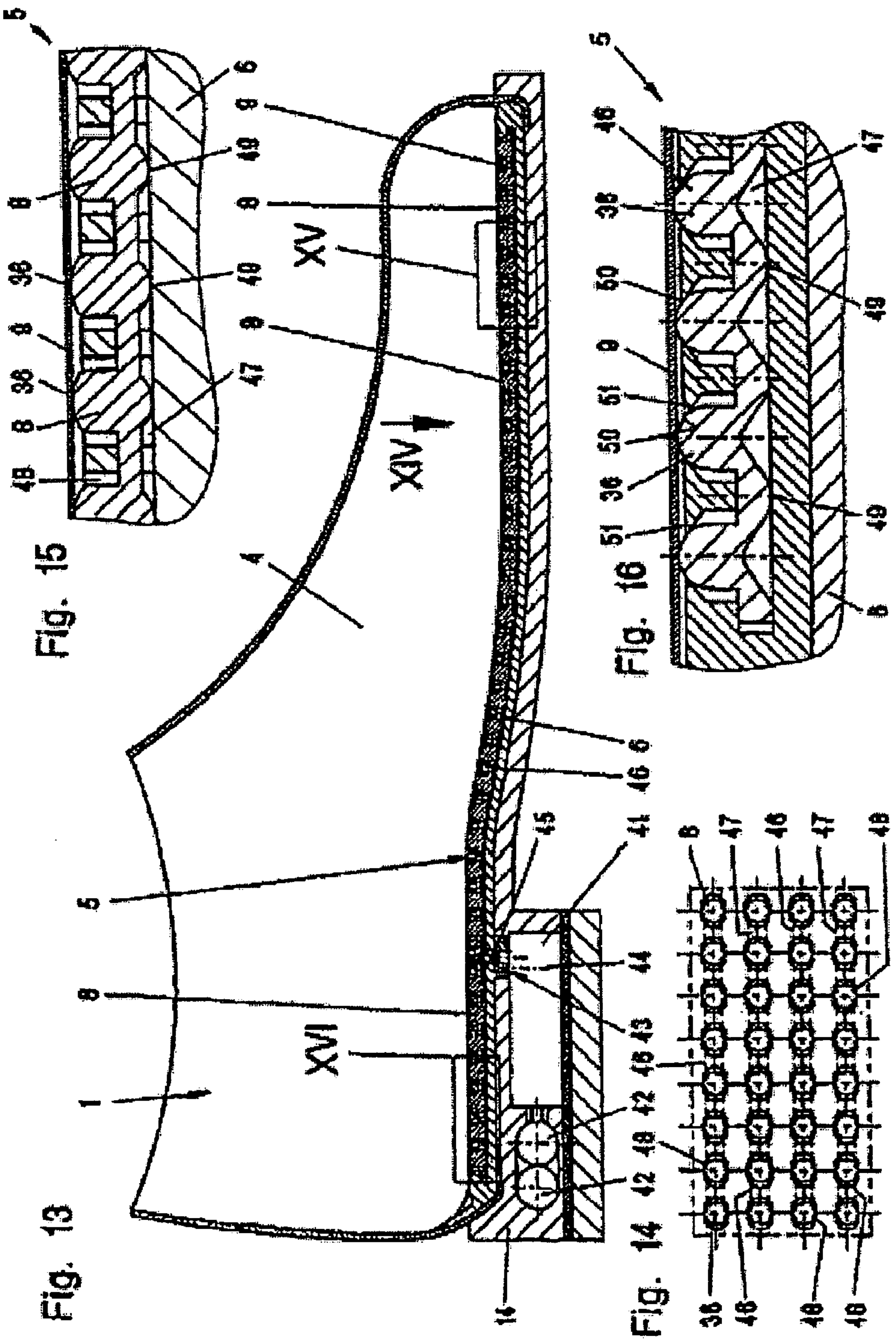

A motor 41 is inserted in the heel 14 in the shoe 1 according to FIGS. 13–15. This motor is operated by appropriate batteries 42. The motor 41 can be turned on by means of a switch that is not shown. However, automatic starting of the motor 41 by loading of the heel 14 is also possible.

The pad 5 with bumps 8 is inserted into the shoe interior 4. The pad is covered on the top side with a flexible protective nonwoven fabric 9. A driver 43 is provided between this pad 5 and the motor 41. A driver bolt 45 is held off-center to the motor axis 44 in the driver. The driver 43 is supported perpendicular to the pad 5 and thus has freedom of movement in the longitudinal direction of the shoe 1 because the driver is located to an extent eccentric to the motor axis 44.

In the longitudinal direction of the shoe 1, the bumps 8 are assembled into a bump band 46 with several bump bands 46 being arranged one next to the other. The base plate 6 of the pad 5 has band recesses 47, in which the bump bands 46 can move. The bumps 8 of the bump bands 46 project with their heads 36 through elongated holes 48, which are aligned in the longitudinal direction of the shoe 1 and whose length corresponds to the diameter of the bumps 8 plus the freedom of movement. The protective nonwoven fabric 9 contacts the bumps 8 and is pressed around the bumps 8 by the foot. The motor 41 moves all bump bands 46 by means of the driver 43. The bands are moved back and forth in alternating longitudinal movements and thus produce a massaging effect. It is, of course, also possible to arrange the bump bands 46 perpendicularly in the shoe 1. Opposite the bump head 36 there is a sliding dome cap 49, with which the bumps 8, and thus the bump bands 46, are supported in a sliding manner on the base plate 6.

FIG. 16 shows an alternative configuration of a bump band 46. The bump head 36 projects out of a bump hole 50. There are diagonals 51 towards the bump hole 50 in both directions of the displacement of the bump band 46. With the motion of the bump band 46, these diagonals allow the bump head 36 to be pushed in and out of the bump pad 5. The material of the bump band 46 is elastic and formed such that the material-specific elastic spring effect presses the bump head 36 out of the bump hole 50.

Figure 17:
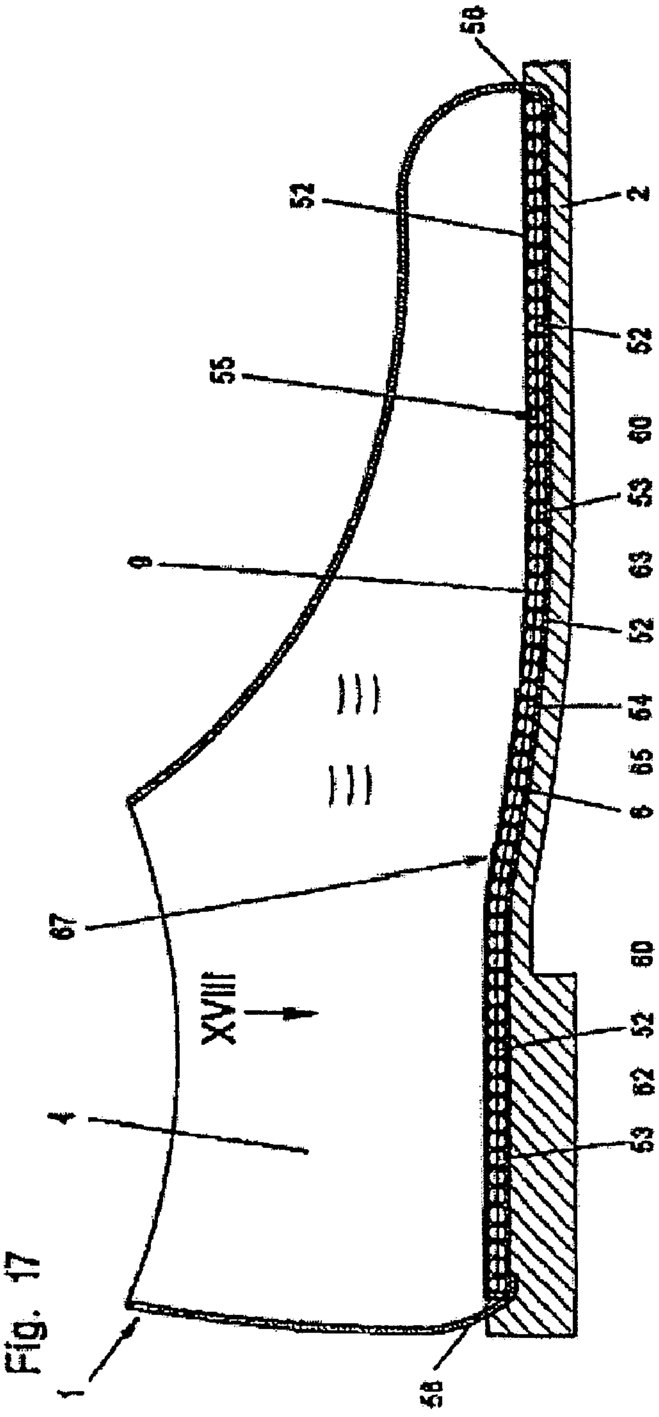
Figure 22:
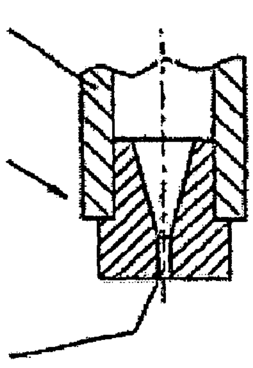
Figure 21:
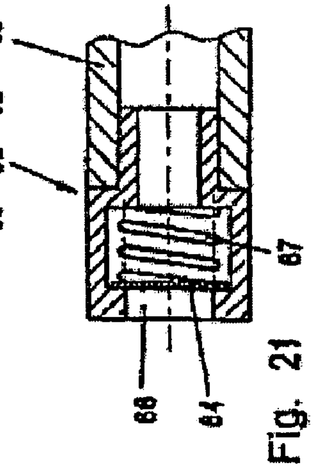
Figures 18, 19, 20:
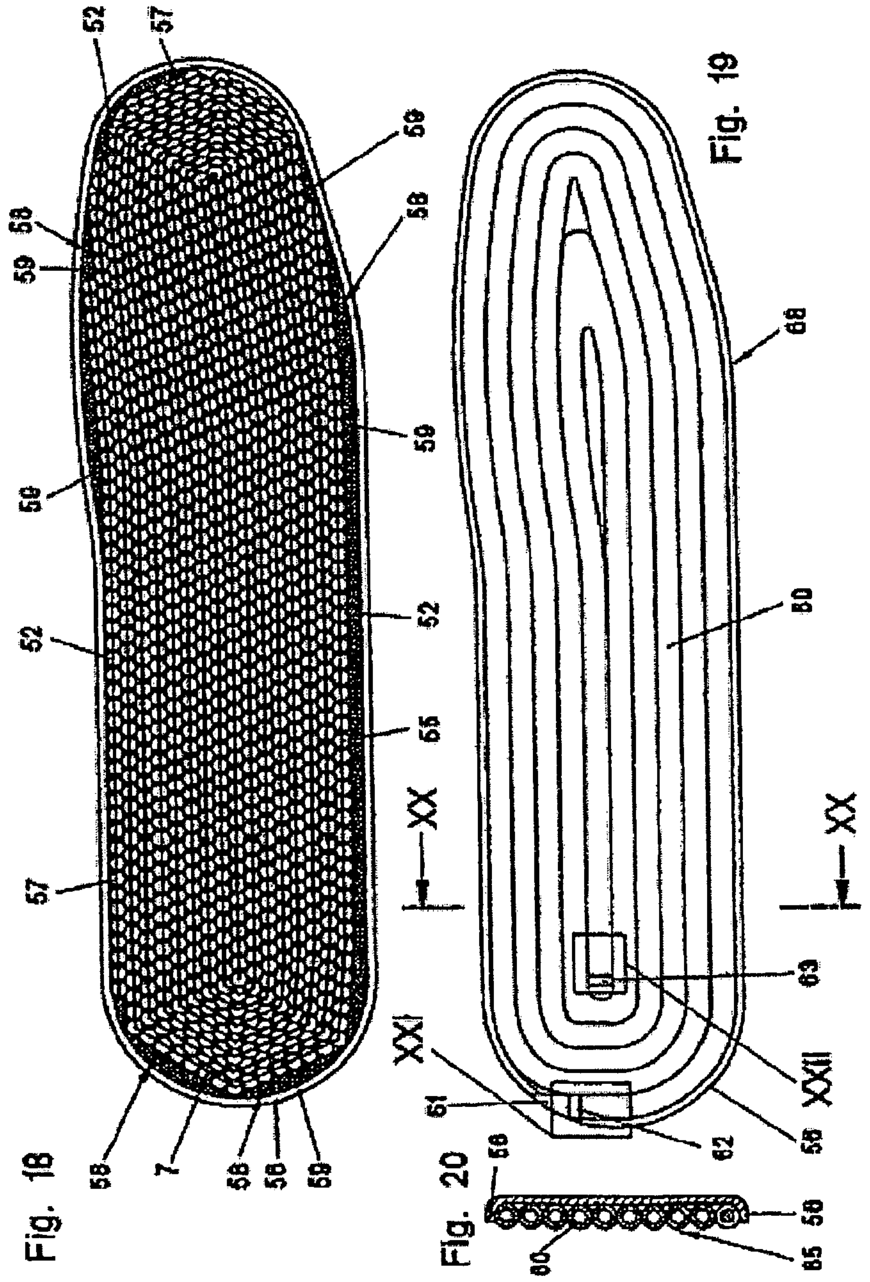

For the shoe according to FIGS. 17 and 18, the pad 67 includes balls 52, which are arranged one next to the other between the base plate 6 and the protective nonwoven fabric 9 and which each have a central through hole 53, through which a thread 54 is passed. The thread thus holds the balls 52 together and forms a ball thread 55, which is placed in the pad 67 in the form of a spiral. A surrounding edge 56 of the base plate 6 aligned in the direction of the shoe interior 4 holds the ball thread 55 in position. Another thread 57 equipped with loose balls 52 is provided in a region, which is not filled by the ball thread 55. This thread 55 [sic; 57] is attached at its ends to the ball thread 55. Thus produces the largest possible arrangement of balls 52 on the base plate 6. For better clarity, the threads 54 and 57 are shown in FIGS. 17 and 18 by a thick, full line. The regions 58 not filled by balls 52 are filled with elastic nonwoven strips 59, which forces the balls 52 to always be close together. Under the loading by a foot, the balls 52 get out of the way, i.e., they slide or slip away from the direct pressure point, which produces a massaging effect.

Another alternative configuration of the shoe 1 is shown in FIGS. 19–22. In the peripheral edge 56 of this pad 68 there is a one-piece, elastic tube 60. Behind the opening 61 of the peripheral edge 56, there is the outer edge of the tube 60, in which an air inlet valve 62 is sealed as a one-way valve. The inner end of the tube 60 is connected to a throttled air outlet 63. In the air inlet valve 62, a spring-loaded pressure plate 64 is present with the spring 65 acting on the pressure plate 64 exhibiting only a weak characteristic curve. The spring can be pulled back for the generation of a low pressure in the tube 60 when pressure is exerted on the tube 60 by a foot, which releases the inlet opening 66 of the air inlet valve 62. The air outlet 63 has an outlet hole 65 that is relatively small in diameter and that acts like a throttle. The air can be discharged from the outlet hole 65 only relatively slowly, whereby under the loading by the foot a counterpressure is always present in the tube 60. This produces a massaging effect, particularly when the foot rolls in the shoe 1.

LIST OF REFERENCE SYMBOLS

1 Shoe
2 Sole
3 Upper leather
4 Shoe interior
5 Pad
6 Base plate
7 Footbed
8 Bump
9 Protective nonwoven fabric
10 Row
11 Pad
12 Ball
13 Transition

14 Heel
15 Feed
16 Unloaded point
17 Valve
18 Chamber
19 Protective plate
20 Heel sole
21 Compressed medium
22 Suction nonwoven fabric
23 Pad
24 Pore
25 Insert
26 Shoe tip
27 Cap
28 Peripheral edge
29 Spring band
30 Arrow direction
31 Foot region
32 Inner side of 6
33 Bottom side of 8
34 Through chamber
35 Hollow section
36 Bump head
37 Pressure cap
38 Elastic disk
39 Raised section
40 Ventilation openings
41 Motor
42 Battery
43 Driver
44 Motor axis
45 Driver bolt
46 Bump band
47 Band recesses
48 Elongated hole
49 Sliding dome cap
50 Bump hole
51 Diagonal
52 Ball
53 Hole
54 Thread
55 Ball thread
56 Edge
57 Thread
58 Region
59 Nonwoven fabric strip
60 Tube
61 Opening
62 Air inlet valve
63 Air outlet
64 Pressure plate
65 Spring
66 Inlet opening
67 Pad
68 Pad

The invention claimed is:

1. Shoe having a foot-massaging effect, comprising:

a sole, a pad which contains a massaging element, wherein said pad includes a flexible base plate adapted to engage the sole and further includes an elastic protective nonwoven fabric connected to the base plate, wherein the massaging element is formed from a plurality of balls, which are arranged loosely and irregularly, or in uniform or offset rows on the base plate; and a heel, wherein said heel contains a valve device, which is connected to an interior portion of the massaging element.

2. Shoe according to claim 1, wherein the balls are embedded in an elastic material or connected together in rows by the elastic material.

3. Shoe according to claim 2, wherein the balls and the elastic material exhibit generally the same Shore hardness values.

4. Shoe according to claim 2, wherein the balls and the elastic material exhibit generally different Shore hardness values.

5. Shoe according to claim 1, wherein the balls are provided on their surface with a sliding layer.

6. Shoe according to claim 1, wherein the valve device is formed as a one-way valve with ventilation openings fanned in an upper portion of said shoe.

7. Shoe according to claim 1, wherein a flexible, expandable chamber is formed in the heel between the valve device and the massaging element.

8. Shoe according to claim 7, wherein the flexible, expandable chamber is separated on a bottom side by a solid protective plate from a lower region of the heel or the sole.

9. Shoe according to claim 1, wherein said pad is formed as an insert for loose insertion into the shoe.

10. Shoe according to claim 1, wherein the pad is filled with balls and has a flexible spring band surrounding the pad on an inner edge of the pad.

11. Shoe according to claim 1, wherein the massaging element includes a ball thread, which consists of a continuous thread with balls arranged loosely in rows which reside in a spiral formation.

12. Shoe according to claim 11, further including at least one additional thread, which includes loose balls and wherein each end of said additional thread is attached to at least one of the base plate or to the ball thread.

13. Shoe according to claim 11, further including a nonwoven fabric strip residing in an edge region of the pad not filled by the balls.

14. Shoe according to claim 1, wherein the massaging element includes side-by-side rows of balls each ball loosely arranged in a line on a continuous thread with the ends of each thread row being attached to the base plate.

15. Shoe according to claim 1, wherein the balls are generally spherical.

16. Shoe having a foot-massaging effect, comprising:

a sole, a pad which contains a massaging element formed from a plurality of balls, which are arranged an a base plate, wherein the balls are not formed integral to the base plate, wherein said pad includes a base plate adapted to engage the sole and further includes an elastic protective nonwoven fabric connected to the base plate; and a heel, wherein said heel includes a valve device, which is connected to an interior portion of the massaging element.

17. Shoe according to claim 16, wherein the balls are embedded in an elastic material or connected together.

18. Shoe according to claim 16, wherein the balls and the elastic protective nonwoven fabric generally exhibit different Shore hardness values.

19. Shoe according to claim 16, wherein the balls and the elastic protective nonwoven fabric generally exhibit the same Shore hardness values.

20. Shoe according to claim 16, wherein the balls are provided on their surface with a sliding layer.

21. Shoe having a foot-massaging effect, comprising:

a sole, a pad which contains a massaging element, wherein said pad includes a flexible base plate adapted to engage the sole and further includes an elastic protective non-woven fabric connected to the base plate, wherein the massaging element is formed from a plurality of balls, which are arranged loosely and irregularly, or in uniform or offset rows on the base plate, wherein the pad is formed as an insert wherein the insert includes a valve device, which is formed as a one-way valve and which is connected to an interior of the insert.

* * * * *

UNITED STATES PATENT AND TRADEMARK OFFICE

CERTIFICATE OF CORRECTION

PATENT NO. : 7,069,672 B2
APPLICATION NO. : 10/450489
DATED : July 4, 2006
INVENTOR(S) : Matthias Hahn It is certified that error appears in the above-identified patent and that said Letters Patent is hereby corrected as shown below:

In Claim 6, column 10, line 16, replace “fanned” with --formed--

In Claim 16, column 10, line 50, replace “arranged an” with --arranged on--

Signed and Sealed this

Twenty-first Day of November, 2006

JON W. DUDAS
*Director of the United States Patent and Trademark Office*